United States Patent [19]

Murphy et al.

[11] Patent Number: 4,749,683

[45] Date of Patent: Jun. 7, 1988

[54] INHIBITION OF GASTRIC ACID SECRETION WITH ALPHA-TRANSFORMING GROWTH FACTOR

[75] Inventors: Richard A. Murphy, Needham, Mass.; James A. Rhodes, Glen Ellyn, Ill.

[73] Assignee: President and Fellows of Harvard College, Cambridge, Mass.

[21] Appl. No.: 914,528

[22] Filed: Oct. 3, 1986

Related U.S. Application Data

[63] Continuation of Ser. No. 694,699, Jan. 25, 1985, abandoned.

[51] Int. Cl.$^4$ .............................................. A61K 37/02
[52] U.S. Cl. ........................................ 514/2; 514/925
[58] Field of Search ................................... 514/2, 925

[56] References Cited

PUBLICATIONS

Sachs, The New England Journal of Medicine, vol. 310, No. 12, Mar. 22, 1984, pp. 785–786.
Marquardt et al., PNAS U.S.A., vol. 80, Aug. 1983, pp. 4684–4688.
Sporn et al., *Science*, vol. 219, 1983, pp. 1329–1331.
Marquardt et al., cited in Chem. Abstracts, vol. 99, 1983, 116315e.
Murphy et al., *Fed. Proc.*, 44(3), 1985, p. 441.
Delarco et al., Proc. Nat. Acad. Sci., vol. 75, pp. 4001–4005, (1978).
Marquardt et al., Science, vol. 223, pp. 1079–1082, (1984).
Bower et al., Experentia, vol. 31, 825–826, (1975).
Konturek et al., Gastroenterology, vol. 81, 438–443, (1981).
Tam et al., Nature, vol. 309, pp. 376–378, (1984).

*Primary Examiner*—J. R. Brown
*Assistant Examiner*—Jacqueline M. Stone

[57] ABSTRACT

Secretion of gastric acid in the stomach of mammals is inhibited by parenteral administration of alpha-transforming growth factor.

2 Claims, No Drawings

INHIBITION OF GASTRIC ACID SECRETION WITH ALPHA-TRANSFORMING GROWTH FACTOR

This invention was made with Government support and the Government has certain rights in the invention.

This is a continuation of application Ser. No. 694,699, filed Jan. 25, 1985, entitled INHIBITION OF GASTRIC ACID, now abandoned.

This invention relates to a method and composition for inhibiting gastric acid secretion in the stomachs of mammals and pertains more specifically to parenteral administration to a mammal of a composition consisting essentially of alpha-transforming growth factor (alpha-TGF) as the active agent together with a pharmaceutically acceptable non-toxic vehicle or carrier therefor.

Alpha-transforming growth factor is a protein which is secreted by transformed mammalian cells in culture as described by Delarco et al., Proc. Nat. Acad. Sci., Vol. 75, pp. 4001–4005 (1978). The protein as secreted by Fisher rat embryo fibroblasts transformed with feline sarcoma virus has been isolated and its primary amino acid sequence has been determined as described in Marquardt et al., Science, Vol. 223, pp. 1079–1082 (1984). In pure form, alpha-TGF stimulates DNA synthesis and growth of cells grown in culture, apparently acting by binding to receptors on cell membranes which also bind epidermal growth factor, a protein which is believed to have broad importance in regulating the growth of mammalian cells and which has been reported to inhibit gastric acid secretion and the formation of gastric ulcers as described in Bower et al., Experentia, Vol. 31, 825–826 (1975) and Konturek et al., Gastroenterology, Vol. 81, 438–443 (1981). A second form of transforming growth factor (called beta-TGF) has also been identified, which is unrelated chemically to alpha-TGF and which is not useful in the present invention.

It has now been found that in addition to its cell growth promoting activity, alpha-TGF is also effective to inhibit acid secretion from the mammalian stomach and is useful as an anti-secretory (anti-ulcer) agent for the stomach.

The alpha-TGF can be used in the form of a composition consisting essentially of alpha-TGF together with any conventional pharmaceutically acceptable non-toxic vehicle or carrier suitable for parenteral administration, such as normal saline, or a polymeric matrix material adapted to provide a slow release of the alpha-TGF to maintain suitable serum levels. Compositions can be administered intravenously, intramuscularly or by percutaneous introduction in any other suitable manner. While the size of the dose is not critical, a dose of 0.1–5 mg/kg body weight/24 hours of alpha-TGF, preferably of the order of 2 mg/kg body weight/24 hours, is suitable and effective.

The following examples are intended to illustrate more fully the nature of the present invention without acting as a limitation upon its scope.

EXAMPLE 1

Alpha-TGF was prepared by conventional solid state protein synthesis as described in Tam et al., Nature, Vol. 309, pp. 376–378 (1984). Purity of the product was established by electrophoresis and by high performance liquid chromatography. Its effect in inhibiting secretion of gastric acid was assayed by the following procedure.

Unfasted female guinea pigs (205–330 g) were killed by cervical dislocation and the stomachs were removed. The antrum was discarded and the stomach was rinsed clean with several washes of mammalian Ringer's solution at 37° C. The stomach was hemisected along the greater and lesser curvatures and the mucosa was separated from the seromuscularis with a pair of fine forceps. Mucosae from both sides were stretched and separately mounted in Lucite Ussing chambers (diameter 1.6 cm) and the assembled chambers were connected to water jacketted gas-lift incubators. The nutrient (submucosal) surface was bathed in 15 ml of a solution containing: 122 mM NaCl, 25.0 mM $NaHCO_3$, 5.0 mM KCl, ½ mM $MgSO_4$, 2.0 mM $CaCl_2$, 1.0 mM $KH_2PO_4$, 20.0 mM glucose, and 100 ug/ml gentamycin sulphate (Garamycin). The solution was gassed with 95% $O_2$-5% $CO_2$ bubbled through distilled water which maintained pH at 7.45–7.55. The luminal (mucosal) surface was bathed in 15 ml unbuffered saline (150 mM NaCl) which was gassed with 100% $O_2$ passed through 500 mM NaOH to remove $CO_2$. Gastric acid secretion was measured by the pH stat method. pH was held at 4.5 with a pH stat coupled to an autoburette and acid secretion was determined by the amount of NaOH necessary to maintain pH in the luminal solution. All solutions were maintained at 37° C. with a heated water circulator. Tissues were initially allowed to stabilize in the chambers a minimum of 2 hours. Saline with or without alpha TGF (60 ng/ml final concentration) was then added to the nutrient bath and the basal rate of acid secretion was monitored for 30 minutes. Twenty-one paired sets of tissue specimens from the same animal were employed, one receiving alpha-TGF, the other serving as control. All tissues were then treated with histamine ($10^{-4}$M) and acid secretion was measured for an additional 3 hours. When calculated in terms of absolute levels of acid secretion, differences between control and TGF-treated tissues were significant ($p<0.05$) at 120, 150, and 180 minutes. The results are shown in Table 1 below.

TABLE 1

TGF-Inhibition of Histamine-Induced Gastric Acid Secretion

|  | Control (mean ± SEM) (uEq./cm²/hr) | TGF-treated (mean SEM) (uEq./cm²/hr) |
| --- | --- | --- |
| 0 time | 1.88 ± 0.23 | 1.80 ± 0.21 |
| 30 min. | 2.25 ± 0.23 | 2.09 ± 0.24 |
| 60 min. | 3.44 ± 0.38 | 2.62 ± 0.35 |
| 90 min. | 3.99 ± 0.33 | 2.97 ± 0.38 |
| 120 min. | 4.10 ± 0.28 | 2.97 ± 0.35 |
| 150 min. | 4.17 ± 0.33 | 3.04 ± 0.37 |
| 180 min. | 4.42 ± 0.24 | 3.16 ± 0.68 |

Results indicate that TGF had no effect on the basal rate of acid secretion (control: 1.88±0.24 uEq./cm²/hr; n=21; TGF: 1.80±0.21 uEq./cm²/hr.)

When acid secretion following histamine as shown in Table 1 is calculated relative to the rate of acid secretion during the 30 minute period prior to histamine treatment, differences between TGF-treated and control tissues, as shown in Table 2, were significant ($p<0.02$) at all time points between 60 and 180 minutes.

TABLE 2

Inhibition of Gastric Acid Release:
Ratio of Pre- and Post Histamine Treatment

|  | Control (mean SEM) | TGF-treated (mean SEM) |
|---|---|---|
| 0 min. | 1.00 ± 0.00 | 1.00 ± 0.00 |
| 30 min. | 1.33 ± 0.09 | 1.17 ± 0.04 |
| 60 min. | 2.09 ± 0.20 | 1.48 ± 0.11 |
| 90 min. | 2.44 ± 0.23 | 1.67 ± 0.12 |
| 120 min. | 2.57 ± 0.24 | 1.68 ± 0.11 |
| 150 min. | 2.89 ± 0.29 | 1.73 ± 0.12 |
| 180 min. | 2.84 ± 0.26 | 1.81 ± 0.27 |

As shown in this Table 2, histamine increased secretion in control tissues 2.09±0.20 (SEM) fold by one hour, 2.58±0.24 fold by two hours, and 2.85±0.26 fold by three hours. During the same time periods, TGF-treated tissues increased only 1.49±0.11, 1.68±0.11, and 1.81±0.27 fold. Differences between the two treatment groups were highly significant ($p<0.02$).

What is claimed is:

1. Method of inhibiting secretion of gastric acid in the stomach of a mammal which comprises administering parenterally to said mammal an effective dose from 0.1 to 5 mg/kg body weight/24 hours of alpha-transforming growth factor.

2. A composition effective for inhibiting secretion of gastric acid in the stomach of a mammal comprising a gastric acid secretion inhibiting amount of alpha-transforming growth factor in combination with a pharmaceutically acceptable non-toxic vehicle or carrier therefor.

* * * * *